United States Patent
Hashmi et al.

(10) Patent No.: US 9,546,119 B2
(45) Date of Patent: Jan. 17, 2017

(54) METHOD FOR REMOVAL OF ORGANIC AMINES FROM HYDROCARBON STREAMS

(71) Applicant: SAUDI BASIC INDUSTRIES CORPORATION, Riyadh (SA)

(72) Inventors: Syed M. Azhar Hashmi, Riyadh (SA); Mohammed H. Al-Hazmi, Riyadh (SA); Abdullah Naffisa, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 271 days.

(21) Appl. No.: 14/350,854

(22) PCT Filed: Oct. 2, 2012

(86) PCT No.: PCT/EP2012/069461
§ 371 (c)(1),
(2) Date: Apr. 10, 2014

(87) PCT Pub. No.: WO2013/053623
PCT Pub. Date: Apr. 18, 2013

(65) Prior Publication Data
US 2014/0336434 A1    Nov. 13, 2014

(30) Foreign Application Priority Data

Oct. 10, 2011    (EP) .................................... 11184464

(51) Int. Cl.
| | |
|---|---|
| *C07C 7/152* | (2006.01) |
| *C07C 11/02* | (2006.01) |
| *C07C 7/148* | (2006.01) |
| *C07C 7/00* | (2006.01) |

(52) U.S. Cl.
CPC ........... *C07C 7/14858* (2013.01); *C07C 7/005* (2013.01); *C07C 7/152* (2013.01); *C07C 11/02* (2013.01)

(58) Field of Classification Search
None
See application file for complete search history.

(56) References Cited

U.S. PATENT DOCUMENTS

| | | |
|---|---|---|
| 3,864,402 A | 2/1975 | Swanson et al. |
| 4,042,490 A | 8/1977 | Suggitt et al. |
| 4,717,553 A | 1/1988 | Turk |
| 5,811,619 A | 9/1998 | Commereuc et al. |
| 6,894,201 B1 | 5/2005 | Schmidt et al. |

FOREIGN PATENT DOCUMENTS

| | | |
|---|---|---|
| EP | 2258674 A1 | 12/2010 |
| WO | 2009095147 A1 | 8/2009 |

OTHER PUBLICATIONS

International Search Report for Application No. PCT/EP2012/069461; Date of Mailing: Nov. 19, 2012; 2 pages.
Written Opinion of the International Searching Authority for Application No. PCT/EP2012/069461; Date of Mailing: Nov. 19, 2012; 6 pages.
Waldman et al., "Isocyanates From Primary Amines and Carbon Dioxide: 'Dehydration' of Carbamate Anions"; J. Chem. Soc., Chem. Commun., 1994, pp. 957-958; 2 pages.

*Primary Examiner* — Tam M Nguyen
(74) *Attorney, Agent, or Firm* — Cantor Colburn LLP

(57) ABSTRACT

The present invention relates to a method for removal of an organic amine from a liquid hydrocarbon stream containing the amine, comprising: a) adding water to the hydrocarbon stream containing the amine, b) bubbling carbon dioxide through the hydrocarbon stream containing the amine, and c) separating a solid phase formed containing the amine from a liquid phase.

18 Claims, No Drawings

METHOD FOR REMOVAL OF ORGANIC AMINES FROM HYDROCARBON STREAMS

CROSS REFERENCE TO RELATED APPLICATIONS

This is the U.S. national stage of application No. PCT/EP2012/069461, filed on Oct. 2, 2012, the disclosure of which is incorporated herein by reference. Priority under 35 U.S.C. §119(a) and 35 U.S.C. §365(b) is claimed from European Application No. 11184464.3, filed Oct. 10, 2011, the disclosure of which is also incorporated herein by reference.

The present invention relates to a method for removal of an organic amine from a liquid hydrocarbon stream containing the amine.

In the chemical industry, processes are often conducted resulting in an outlet stream product or a feed stream to a process unit comprising hydrocarbons and amines. An example thereof is the outlet stream from a reactor utilized for preparing linear alpha-olefins (LAO) by oligomerization of ethylene. The linear alpha-olefins produced are then separated into different fractions for further use or marketing. Often, an amine is added during the oligomerization process or is added into a reactor outlet piping system. Such processes are, for example, disclosed in U.S. Pat. No. 5,811,619 or WO2009/095147. The problem of corrosion of stainless steel trays of distillation columns in LAO plants was due to the formation of organic chlorides.

In case of LAO production, without an efficient removal of the amines, the LAO-product with a certain concentration of the amine has to be marketed under consideration of its amine content, which may restrict its applicability for certain downstream processes. For example, the amine could represent a poison in processes with sensitive catalytic reactions.

In many cases, it is difficult to remove the organic amine from a hydrocarbon stream or fractions thereof by distillation as the boiling points of the amine and the hydrocarbon stream, especially fractions thereof, are very close. For example, n-dodecylamine (DDA) is often added in an oligomerization process, which after the product fractionation finally ends up in the $C_{14}$-LAO-product fraction. Since DDA has a boiling point close to the $C_{14}$-product, it can not be removed by distillation. The same is true for the addition of 2-ethyl-hexyl-amine which has a very close boiling point to $C_{10}$-linear alpha-olefins.

Another general approach for removal of an organic amine from a hydrocarbon stream is to react the amine containing hydrocarbon stream with an acid to convert the amine into an amine salt. Subsequently, the amine salt can be extracted into an aqueous phase.

However, this method results in plants with considerable investment cost under utilization of acid-resistant materials of construction.

In the patent U.S. Pat. No. 4,717,553 a process for removing amines having normal boiling points under 100° C. from a gas stream by passing the gas stream through activated carbon in the presence of carbon dioxide is disclosed.

It is therefore an object of the present invention to provide a method for removal of an organic amine from a liquid hydrocarbon stream containing the amine which overcomes the drawbacks of the prior art. Especially, a method shall be provided enabling that the hydrocarbon product can be marketed without any restrictions due to its amine content.

Further, a method shall be provided wherein the amine can be easily removed from the hydrocarbon stream and recycled afterwards.

It is also an object of the present invention to provide a method for removal of organic amine from hydrocarbon streams containing the amine which avoids the requirements of high investment costs and the use of acid resistant materials for construction.

These objects are achieved by a method for removal of an organic amine from a liquid hydrocarbon stream containing the amine, comprising the steps:
a. adding water to the hydrocarbon stream containing the amine,
b. bubbling carbon dioxide through the hydrocarbon stream containing the amine, and
c. separating a solid phase formed containing the amine from a liquid phase.

In one embodiment, the hydrocarbon stream containing the amine is an outlet-stream from a reactor for preparing linear alpha-olefins (LAO) or a fraction of such an outlet stream.

In another preferred embodiment, the organic amine is an amine, which is liquid at room temperature and normal pressure.

In one embodiment, the organic amine has a boiling point higher than 100° C. The inventive method is especially suitable for the removal of liquid amines having boiling points of above 100° C., but being still liquid at room temperature and normal pressure. Respective amines have preferably strong basicity, compared to gaseous mono-, di- and triethylamines. Thus, they easily react without any catalysts, such as activated carbon.

More preferably, the organic amine is 2-ethyl-hexyl-amine and/or n-dodecylamine.

In one embodiment, the water is added in an amount from 5-70% by weight relative to the total amount of hydrocarbon stream, preferably 15-60%, more preferably 25-50%.

In another embodiment, bubbling is carried out for 5-60 minutes (min), preferably 10-50 min, more preferably 20-40 min.

Preferably, the flow rate of carbon dioxide is in a range from 50-150 cubic centimeters per minute (cc/min), based on the total amount of liquid hydrocarbon mixture present in the reactor.

Even preferred, the added water is at least once replaced, at least partially, by fresh water while bubbling carbon dioxide through the hydrocarbon stream.

Replacement of water by fresh water was found to facilitate the separation of the amines from the liquid hydrocarbon stream.

In another preferred embodiment, separating is carried out by filtration.

Also preferred, the method, especially separating, is carried out in a temperature range from 30-80° C., more preferred 50-80° C. At very low temperatures, such as 15-25° C., the separation of solid formed is not satisfying.

Even preferred, the amine can be recovered from the solid phase by heating the solid phase in water or in an aqueous solution.

Finally it is preferred that the liquid hydrocarbon stream contains linear alpha-olefins (LAO), preferably $C_8$-$C_{10}$ linear alpha-olefins, and optionally organic solvent.

Surprisingly, it was found that the inventive method for removing an organic amine from a hydrocarbon stream containing the amine provided finally a hydrocarbon product which can be marketed without any restrictions due to its amine content. In detail, the amine concentration of the hydrocarbon stream can be reduced from about 5 to 6 weight percent (wt.-%) to less than 0.5 parts per million (ppm).

Further, it was surprisingly found that the method of the present invention allows easy removal and recycling of the amine.

Finally, the inventive method can be carried out without utilizing any special acid-resistant equipment. Especially, it is obvious that the inventive method thus offers savings on investment and maintenance costs and increases plant reliability.

In the inventive method, it is assumed that the organic amine does react with the carbon dioxide to form carbamate zwitter ions, as primary and secondary amines rapidly react with carbon dioxide. The addition of water, especially in high amounts, increases the sorption capacity and rate manifold. The reaction of organic amine and carbon dioxide may be according to the following formula:

$$2\ RNH_2 + CO_2 \rightarrow RNH_3^+ {}^-O_2CNHR$$

wherein R is any suitable alkyl group.

The solid carbamate obtained can be easily separated from the liquid hydrocarbon stream or for example by filtration, without any specific requirements to be considered to separate organic and aqueous phases. However, very hot water for washing the solid phase should be avoided.

It is obvious to one skilled in the art that the hydrocarbon stream can contain more than just one amine. Thus, the method is not limited to the removal of just one single organic amine but also relates to the removal of two or more different organic amines from the hydrocarbon stream.

In a most preferred embodiment of the invention, the method for removal of an organic amine from a hydrocarbon stream containing the amine according to the invention is embedded in a method for preparing linear alpha-olefins (LAO) by oligomerization of ethylene, preferably in the presence of solvent and catalyst, comprising the steps:
  i) feeding ethylene in an oligomerization reactor,
  ii) oligomerizing the ethylene in the reactor,
  iii) removing a reactor outlet stream comprising linear alpha-olefins from the reactor via a reactor outlet piping system,
  iv) transferring the reactor outlet stream to a catalyst deactivation and removal step, and
  v) deactivating and removing the catalyst from the reactor outlet stream, wherein at least one organic amine is added into the oligomerization reactor and/or into the reactor outlet piping system The reactor outlet stream or a fraction thereof can be taken as a hydrocarbon stream in the present invention.

It can be particularly advantageous to integrate a process utilizing the method of the present invention in another process generating carbon dioxide, for example, the ethylene oxide process.

Additional features and advantages of the present invention will become apparent in the following detailed description on the basis of examples.

EXAMPLE 1

A 500 milliliter (ml) 3 neck flask was charged with about 50 grams (g) of a typical fraction containing mostly C-7 (32%), C-10 (24%), C-12 (17%), C-13 (3%), C-14 (10%) and other higher C-15+ components (~10%) from the process for preparing linear alpha-olefins and containing about 2.5% of 2-ethylhexyl-amine. To the flask was then added 25-50% by weight of water relative to the total amount of organic material. Next was added 25% by weight of toluene relative to the total amount of organic material. The resulting mixture was stirred and heated up to 70° C. Carbon dioxide was bubbled through the mixture with a flow rate of about 100 cc/min for 60 min. In Table 1 the analysis results of the mixture is shown. Samples were taken from the organic phase, afterwards the mixture was filtered through a Buchner funnel. The filtrate obtained that way was analyzed utilizing GC-MS.

EXAMPLE 2

A 500 ml 3 neck flask was charged with about 50 g of a typical fraction containing mostly C-7 (32%), C-10 (24%), C-12 (17%), C-13 (3%), C-14 (10%) and other higher C-15+components (~10%) from the process for preparing linear alpha-olefins and containing about 2.5% of 2-ethylhexyl-amine. To the flask was then added 25% by weight of toluene relative to the total amount of organic material. The resulting mixture was stirred and heated up to 70° C. Carbon dioxide was bubbled through the mixture with a flow rate of about 100 cc/min for 60 min. In Table 1 the analysis results of the mixture as determined by GC-MS is shown. The results showed that the amine was not removed and also the concentration of amine does not change.

EXAMPLE 3

A 500 ml 3 neck flask was charged with about 50 g of a typical fraction containing mostly C-7 (32%), C-10 (24%), C-12 (17%), C-13 (3%), C-14 (10%) and other higher C-15+components (~10%) from the process for preparing linear alpha-olefins and containing about 2.5% of 2-ethylhexyl-amine. The resulting mixture was stirred and heated up to 70° C. Carbon dioxide was bubbled through the mixture with a flow rate of about 100 cc/min for 60 min. In Table 1 the analysis results of the mixture as determined by GC-MS is shown. The results showed that the amine was not removed and also the concentration of amine does not change.

The GC analytical data can be summarized in Table 1 below.

TABLE 1

| GC Analytical Data | | | | |
|---|---|---|---|---|
| Component | Unit | Example 1 | Example 2 | Example 3 |
| Amine | % | 0.0 | 2.5 | 2.5 |
| C-7 | % | 29.3 | 34 | 33 |
| C-8 | % | <0.1 | <0.1 | <0.1 |
| C-9 | % | 0.5 | 0.5 | 0.3 |
| C-10 | % | 24.7 | 22.5 | 23 |
| C-11 | % | 0.7 | 0.7 | 0.7 |
| C-12 | % | 17.7 | 17.0 | 16.7 |
| C-13 | % | 2.9 | 3.0 | 3.0 |
| C-14 | % | 14.0 | 10.7 | 11 |
| C-15 | % | 3.1 | 2.5 | 2.3 |
| C-16 | % | 0.7 | 1.0 | 1.0 |
| C-17 | % | 1.0 | 1.0 | 1.2 |
| C-18 | % | 2.1 | 2.1 | 2.4 |
| C-20 | % | 1.5 | 1.2 | 1.4 |
| C-22+ | % | 1.0 | 1.0 | 1.2 |

(Example-1: LAO + Amine + Water + Toluene + Carbon dioxide
Example-2: LAO + Amine + Toluene + Carbon dioxide
Example-3: LAO + Amine + Carbon dioxide)

As can be taken, after a reaction time of 60 min, no amine can be detected at all in the organic product of the inventive method.

The features disclosed in the foregoing description in the figure or in the claims may, both separately and in combination thereof, the material for realizing the invention in diverse forms thereof.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

The invention claimed is:

1. A method for removal of an organic amine from a liquid hydrocarbon stream containing the amine, comprising:
    a) adding water to the hydrocarbon stream containing the amine,
    b) bubbling carbon dioxide through the hydrocarbon stream containing the amine, and
    c) separating a solid phase formed containing the amine from a liquid phase.

2. The method according to claim 1, wherein the hydrocarbon stream containing the amine is an outlet stream from a reactor for preparing linear alpha-olefins (LAO) or a fraction of such an outlet stream.

3. The method according to claim 1, wherein the organic amine is an amine, which is liquid at room temperature and normal pressure.

4. The method according to claim 1, wherein the organic amine has a boiling point higher than 100° C.

5. The method according to claim 1, wherein the water is added in an amount from 5-70% by weight relative to the total amount of hydrocarbon stream.

6. The method according to claim 1, wherein bubbling is carried out for 5 to 60 min.

7. The method according to claim 1, wherein the flow rate of carbon dioxide is in a range from 50 to 150 cc/min based on the total amount of liquid hydrocarbon mixture present in the reaction.

8. The method according to claim 1, wherein the added water is at least once replaced, at least partially, by fresh water while bubbling carbon dioxide through the hydrocarbon stream.

9. The method according to claim 1, wherein separating is carried out by filtration.

10. The method according to claim 1, wherein the method is carried out in a temperature range from 30-80° C.

11. The method according to claim 1, wherein the amine is recovered from the solid phase by heating the solid phase in water or in an aqueous solution.

12. The method according to claim 1, wherein the liquid hydrocarbon stream contains linear alpha-olefins (LAO), preferably $C_8$-$C_{10}$ linear alpha-olefins, and optionally organic solvent.

13. The method of claim 4, wherein the organic amine is 2-ethyl-hexyl-amine and/or n-dodecylamine.

14. The method of claim 5, wherein, wherein the water is added in an amount of 15-60%.

15. The method of claim 14, wherein the water is added in an amount of 25-50%.

16. The method of claim 6, wherein bubbling is carried out for 10 to 50 min.

17. The method of claim 16, wherein bubbling is carried out for 20 to 40 min.

18. The method of claim 10, wherein the method is carried out in a temperature range of 50-80° C.

\* \* \* \* \*